(12) United States Patent
Brown et al.

(10) Patent No.: US 6,270,486 B1
(45) Date of Patent: *Aug. 7, 2001

(54) ABSORBENT INTERLABIAL DEVICE

(75) Inventors: Pamela Jean Brown, Maineville; Thomas Ward Osborn, III, Cincinnati, both of OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/071,425

(22) Filed: May 1, 1998

Related U.S. Application Data (63) Continuation-in-part of application No. 08/876,206, filed on Jun. 16, 1997, now abandoned.

(51) Int. Cl.$^7$ .............................. A61F 13/15; A61F 13/20
(52) U.S. Cl. ............... 604/385.17; 604/358; 604/385.01; 604/904
(58) Field of Search ..................................... 604/358, 365, 604/367, 383, 385.01, 385.17, 904

(56) References Cited

U.S. PATENT DOCUMENTS

| | | | |
|---|---|---|---|
| 2,662,527 | * 12/1953 | Jacks | 604/385.01 |
| 2,771,882 | * 11/1956 | Leupold | 604/385.01 |
| 3,420,235 | * 1/1969 | Harmon | 604/385.01 |
| 3,690,321 | * 9/1972 | Hirschman | 128/285 |
| 3,726,277 | * 4/1973 | Hirschman | 128/285 |
| 3,857,394 | 12/1974 | Alemany . | |
| 3,905,372 | * 9/1975 | Denkinger | 128/285 |
| 3,983,873 | * 10/1976 | Hirschman | 128/285 |
| 4,095,542 | * 6/1978 | Hirschman | 112/262 |
| 4,142,476 | * 3/1979 | Hirschman | 112/262 |
| 4,175,561 | 11/1979 | Hirschman . | |
| 4,196,562 | * 4/1980 | Hirschman | 53/450 |

(List continued on next page.)

FOREIGN PATENT DOCUMENTS

| | | |
|---|---|---|
| 01 161 663 A1 | 11/1985 | (EP) . |
| 01 162 451 A1 | 11/1985 | (EP) . |
| 0 685 215 A1 | 12/1995 | (EP) . |
| 2 420 339 | 10/1979 | (FR) . |
| 588689 | 5/1947 | (GB) . |
| 754481 | 8/1956 | (GB) . |
| 2 227 666 A | 8/1990 | (GB) . |
| 2 238 286 A | 5/1991 | (GB) . |
| 09-099009 | 4/1997 | (JP) . |
| WO 96/07379 | 3/1996 | (WO) . |
| WO 97/18784 | 5/1997 | (WO) . |
| WO 98/08475 | 3/1998 | (WO) . |

*Primary Examiner*—John G. Weiss
*Assistant Examiner*—Michele Kidwell
(74) *Attorney, Agent, or Firm*—Matthew P Fitzpatrick; Kevin C Johnson; Steven W Miller

(57) ABSTRACT

An absorbent interlabial device worn by female wearers for catamenial purposes, incontinence protection, or both, is disclosed. The absorbent interlabial device of the present invention includes a liquid pervious topsheet, a liquid impervious backsheet, and an absorbent core positioned between the two. The length of the device is between about 60 mm and about 130 mm. The width is between about 25 mm and 50 mm. The device has an axis of preferred bending along its longitudinal centerline. When folded along the axis and inserted into the wearer's interlabial space, the topsheet maintains contact with the walls of the wearer's labia. A method of using a system of feminine hygiene products is also disclosed. The system includes the use of an absorbent interlabial device in combination with a sanitary napkin. The absorbent interlabial device of the present invention may also be used in combination with an absorbent tampon. The absorbent interlabial device may be packaged in a common package with a sanitary napkin or a tampon as a feminine hygiene kit.

21 Claims, 5 Drawing Sheets

U.S. PATENT DOCUMENTS

| | | |
|---|---|---|
| 4,212,301 | 7/1980 | Johnson . |
| 4,433,972 | 2/1984 | Malfitano . |
| 4,595,392 * | 6/1986 | Johnson et al. ...................... 604/385 |
| 4,627,848 | 12/1986 | Lassen et al. . |
| 4,631,062 * | 12/1986 | Lassen et al. ........................ 604/385 |
| 4,673,403 * | 6/1987 | Lassen et al. ........................ 604/385 |
| 4,892,528 * | 1/1990 | Suzuki et al. ..................... 604/385.2 |
| 4,925,453 | 5/1990 | Kannankeril . |
| 5,019,069 * | 5/1991 | Klemp ................................. 604/387 |
| 5,057,096 * | 10/1991 | Faglione ............................ 604/385.1 |
| 5,074,855 * | 12/1991 | Rosenbluth et al. ............. 604/385.1 |
| 5,169,394 | 12/1992 | Jean . |
| 5,196,247 * | 3/1993 | Wu et al. ............................... 428/43 |
| 5,217,803 * | 6/1993 | McBride et al. ...................... 424/323 |
| 5,230,119 | 7/1993 | Woods et al. . |
| 5,290,262 | 3/1994 | Vukos et al. . |
| 5,300,058 * | 4/1994 | Goulait et al. ........................ 604/391 |
| 5,336,208 * | 8/1994 | Rosenbluth et al. .................. 604/329 |
| 5,484,429 * | 1/1996 | Vukos et al. ....................... 604/385.1 |
| 5,573,523 | 11/1996 | Whalen et al. . |
| 5,575,047 | 11/1996 | Gerstenberger et al. . |
| 5,672,165 | 9/1997 | Belecky et al. . |
| 5,702,380 | 12/1997 | Walker . |
| 5,762,644 * | 6/1998 | Osborn, III et al. ............. 604/385.1 |
| 5,771,524 | 6/1998 | Woods et al. . |
| 5,884,771 | 3/1999 | McCormick . |
| 5,885,265 | 3/1999 | Osborn, III et al. . |
| 5,895,381 * | 4/1999 | Osborn, III ....................... 604/385.1 |
| 5,928,452 * | 7/1999 | McFall et al. ........................ 156/269 |
| 6,033,391 * | 3/2000 | Osborn, III et al. ............. 604/385.1 |
| 6,045,544 * | 4/2000 | Hershberger et al. ............ 604/385.1 |

\* cited by examiner

ABSORBENT INTERLABIAL DEVICE

CROSS REFERENCE TO RELATED APPLICATIONS

This is a continuation-in-part of application Ser. No. 08/876,206, filed on Jun. 16, 1997, now abandoned.

FIELD OF THE INVENTION

This invention relates to absorbent devices, and more particularly to an improved absorbent device that is worn interlabially by female wearers for catamenial purposes, incontinence protection, or both.

BACKGROUND OF THE INVENTION

All manner and variety of absorbent articles configured for the absorption of body fluids such as menses, urine and feces are well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953, and U.S. Pat. No. 4,631,062, entitled "Labial Sanitary Pad", issued to Lassen, et al. on Dec. 23, 1986.

Interlabial pads have the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. Nos. 5,074,855 and 5,336,208 issued to Rosenbluth, et al. on Dec. 24, 1991 and Aug. 9, 1994 respectively, and U.S. Pat. No. 5,484,429 issued to Vukos, et al. on Jan. 16, 1996. A commercially available interlabial device is the "FRESH 'N FIT PADETTE" (also known as "INSYNC" or "INSYNC MINIFORM") interlabial pad which is marketed by Athena Medical Corp. (now known as A-Fem) of Portland, Oreg. and described in U.S. Pat. Nos. 3,983,873 and 4,175,561 issued to Hirschman on Oct. 5, 1976 and Nov. 27, 1979, respectively.

Many of these devices have not met with great commercial success, however. There are drawbacks associated with all of the above products. For example, the device described in the Delaney patent does not appear to be capable of an easy and comfortable insertion, due to the possibility of the layers of absorbent material opening up during insertion. The commercially available "PADETTE" ( or "IN-SYNC") interlabial device suffers from the disadvantage that many consumers find it difficult to insert properly and may cause some consumers discomfort especially if not properly inserted. Even when such a device is properly inserted, it may tend to allow by-pass flow around its edges. Such flow can cause body soiling or panty soiling which many consumers find unacceptable. Additionally, previously known interlabial devices such as the "PADETTE" interlabial pad may not reliably cover the urethra and/or the vaginal introitus during all body movements (e.g. when the wearer is squatting). Such products may also not be reliably expelled when the wearer urinates.

Therefore, a need exists for an improved interlabial device which will reduce the incidence of body and panty soiling when used. Such a device should be easy to insert and be comfortable during wear. A need exists for an interlabial device which also covers the walls of the wearer's labia throughout a range of body motions and reliably covers the vaginal introitus and preferably also the urethra during such motions. A need also exists for an improved absorbent interlabial device which may be used as part of a system of feminine hygiene protection or with a feminine hygiene kit.

SUMMARY OF THE INVENTION

This invention relates to absorbent devices, and more particularly to an improved absorbent device that is insertable into the interlabial space of a female wearer for catamenial purposes, incontinence protection, or both.

The absorbent interlabial device of the present invention comprises a liquid pervious topsheet, a liquid impervious backsheet which is joined to the topsheet, and an absorbent core positioned between the topsheet and backsheet. The length of the absorbent interlabial device is greater than about 60 mm and less than about 130 mm. The width of the device is between about 25 and about 50 mm. The width and length of the device each exceed its thickness. Additionally, the device comprises an axis of preferred bending, preferably located generally along the longitudinal centerline of the device. When the device is folded along this axis and inserted into the wearer's interlabial space, the topsheet maintains contact with the walls of the wearer's labia.

In a preferred embodiment, the length of the device may be between about 90 and about 105 mm. Preferably, the liquid pervious topsheet may be constructed of rayon or needle punched rayon. The absorbent core may also be constructed of rayon, cotton, or a blend of rayon and cotton. The backsheet of the absorbent interlabial device is preferably water dispersible. Preferably, the device comprises biodegradable materials. A tab may be attached to the backsheet of the device to facilitate insertion and optional removal of the device with the fingers.

The present invention also relates to a method of using an absorbent interlabial device, such as the absorbent interlabial device described above, as part of a system of feminine hygiene products. The method comprises the steps of inserting an interlabial device into the interlabial space of the wearer, placing a sanitary napkin in the crotch portion of a panty-type undergarment, then pulling the undergarment into its usual wearing position without removing the sanitary napkin from the undergarment or the interlabial device from the wearer's interlabial space such that the sanitary napkin rests adjacent the pudendal region of the wearer and the interlabial device and the sanitary napkin are worn simultaneously. In preferred methods of the present invention, the method may further include the steps of removing the interlabial device prior to urination then, subsequent to urination, inserting a new interlabial device which is worn simultaneously with the sanitary napkin. Optionally, the interlabial device may be expelled by urination, then a second interlabial device may be inserted into the wearer's interlabial space and worn simultaneously with the sanitary napkin.

In another aspect of the present invention, the invention comprises a feminine hygiene kit. The kit is comprised of a sanitary napkin and an absorbent interlabial device packaged in a common package. Such a kit facilitates use of a system of feminine hygiene products such as in the method described above. The sanitary napkin and interlabial device are each adapted such that they may be worn simultaneously. Preferably, the absorbent interlabial device included in the kit has all of the preferred features of the absorbent interlabial device described above.

The absorbent interlabial device of the present invention may also be used as part of a system of feminine hygiene products in conjunction with an absorbent tampon. Such a method comprises the steps of inserting a tampon into the vaginal cavity of the wearer, inserting an absorbent interlabial device into the interlabial space of the wearer, and wearing the tampon and the absorbent interlabial device simultaneously for a period of time. The absorbent interlabial device used in such a method comprises a liquid pervious topsheet, and liquid impervious backsheet joined to said topsheet, and an absorbent core positioned between the two.

Another feminine hygiene kit comprises the absorbent interlabial device of the present invention packaged in a common package with an absorbent vaginal tampon. The absorbent interlabial device comprises a liquid pervious topsheet, a liquid impervious backsheet joined to the topsheet, and an absorbent core positioned between the topsheet and the backsheet. The absorbent interlabial device is adapted to be worn within the interlabial space of the wearer wherein at least half of the device resides within such interlabial space. Each of the absorbent vaginal tampon and the absorbent interlabial device are adapted such that both may be worn simultaneously.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
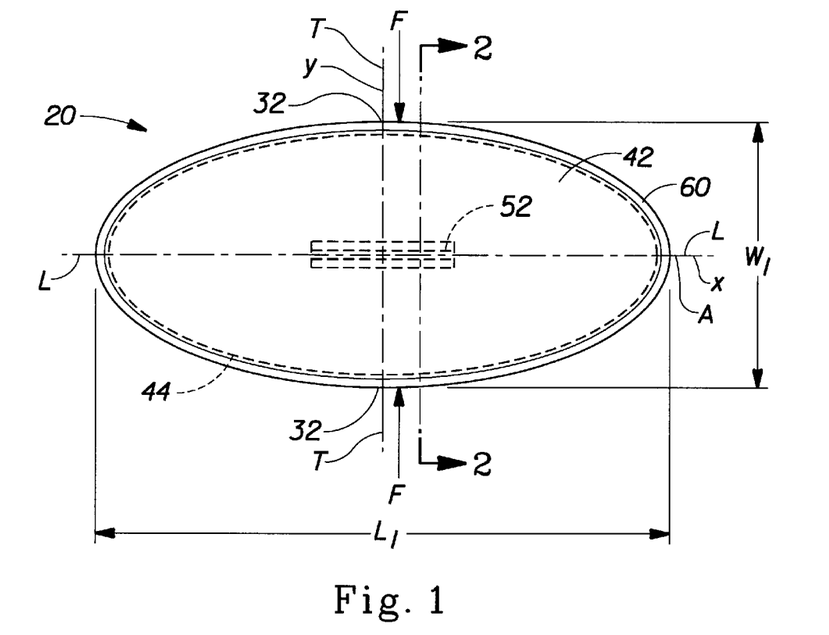
FIG. 1 is a top plan view of the absorbent interlabial device of the present invention.
Figure 2:
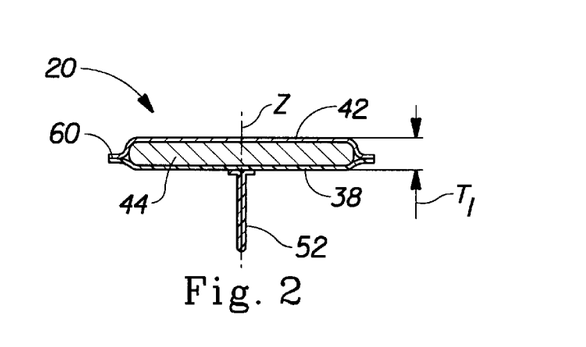
FIG. 2 is a cross sectional view of the absorbent interlabial device of the present invention, taken along line 2—2 of FIG. 1.
Figure 3:
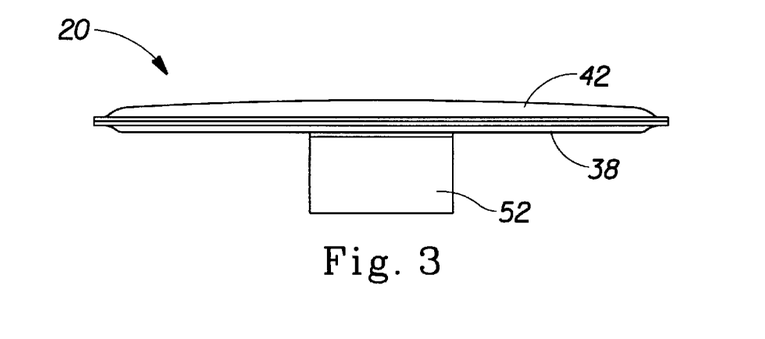
FIG. 3 is a side view of the absorbent interlabial device of the present invention.

The present invention is directed to an absorbent interlabial device. FIGS. 1–3 shows one embodiment of an absorbent interlabial device, interlabial device 20. The present invention, however, is not limited to a structure having the particular configuration shown in the drawings.

As used herein the term "absorbent interlabial device" refers to a structure which has at least some absorbent components, and which is specifically configured to reside within the interlabial space of a female wearer during use. When the absorbent interlabial device 20 is properly sized for an individual wearer, more than half of the entire absorbent interlabial device 20 of the present invention resides within such interlabial space. Preferably substantially the entire absorbent interlabial device 20 resides within such interlabial space, and more preferably the entire absorbent interlabial device 20 resides within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labia minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at 1025–1027.

The absorbent interlabial device 20 shown in FIG. 1 has a longitudinal centerline L which runs along the "x" axis. The term "longitudinal", as used herein, refers to a line, axis or direction in the plane of the interlabial device 20 that is generally aligned with (e.g., approximately parallel to) a vertical plane which bisects a standing wearer into left and right body halves when the interlabial device 20 is worn. The terms "transverse," "lateral," or "y direction" as used herein, are interchangeable, and refer to a line axis or direction that is generally perpendicular to the longitudinal direction. The lateral direction is shown in FIG. 1 as the "y" direction. The absorbent interlabial device 20 shown in FIG. 1 also has a transverse centerline T. The "z" direction, shown in FIG. 2, is a direction parallel to the vertical plane described above. The term "upper" refers to an orientation in the z-direction toward the wearer's head. "Lower" or downwardly is toward the wearer's feet.

As shown in FIGS. 1–2, the interlabial device comprises at least a liquid pervious topsheet 42, a liquid impervious backsheet 38 joined to the topsheet 42, and an absorbent core 44 positioned between the topsheet 42 and the backsheet 38. The interlabial device 20 must be of a suitable size and shape that allows at least the majority of the device 20 to fit comfortably within the wearer's interlabial space and to cover the wearer's vaginal orifice, and preferably also the wearer's urethra. The interlabial device 20 at least partially blocks, and more preferably completely blocks and intercepts the flow of menses, urine, and other bodily exudates from the wearer's vaginal orifice and urethra.

The size of the interlabial device 20 is important to its comfort and effectiveness. The length of the absorbent interlabial device 20 is measured along the longitudinal centerline L in the longitudinal direction (or "x"-direction). The absorbent interlabial device 20 preferably has a length $L_1$ which is greater than about 60 mm and less than about 130 mm. More preferably, the length $L_1$ is between about 90 mm and about 105 mm. The width of the interlabial device 20 is measured along the transverse centerline T in the transverse direction (or "y"-direction). The absorbent interlabial device 20 preferably has a width $W_1$ which is between about 25 mm and about 50 mm. The thickness (or caliper) is the "z"-direction dimension of the device 20. Caliper measurements given herein were measured using an AMES gage with a 0.25 psi (1.7 kPa) (gauge) load and a 0.96 inch (2.44 cm) diameter foot. Those skilled in the art will recognize that if a 0.96 inch (2.44 cm) diameter foot is not appropriate for a particular sample size, the foot size may be varied while the load on the gauge is accordingly varied to maintain a confining pressure of 0.25 psi (1.7 kPa) (gauge). The caliper $T_1$ of the absorbent interlabial device 20 is less than the width $W_1$ and the length $L_1$ of the device 20. Preferably the caliper $T_1$ of the absorbent interlabial device 20 is less than or equal to about 8 mm, more preferably the caliper $T_1$ is less than about 6 mm, and even more preferably less than about 4 mm.

Construction of the absorbent interlabial device 20 according to the particular size parameters given above results in a product with increased comfort and effectiveness compared to previous interlabial devices. For example, many women find interlabial pads which are shorter than the absorbent interlabial device 20 of the present invention (such as previous interlabial pads) to be difficult to position properly within the interlabial space. Even if such pads are positioned properly they have an increased tendency to allow by-pass flow of body exudates around the edges of the pad. Additionally, previous pads were not equipped with a liquid impervious backsheet. These pads, therefore could allow body and panty soiling as a result of contact with the bottom surface of the pad.

The interlabial device 20 is preferably provided with sufficient absorbency to absorb and retain the exudates discharged from the wearer's body. The capacity of the product, however, is dependent at least partially upon the physical volume of the absorbent interlabial device 20. The absorbent interlabial device preferably has a capacity of at least about 1 g of 0.9% by weight saline solution, and may have a capacity of up to about 30 g by using absorbent gels or foams that expand when wet. Capacities may typically range from about 2 to about 10 grams, for saline. Preferably, the capacity of the device 20 is greater than about 6 g for saline. Those skilled in the art will recognize that the capacity for absorption of body exudates such as menses will typically be smaller than the capacities given above for absorption of saline. A method for measuring absorbent capacity is described in the Test Methods section, below. Since the interlabial space can expand, larger volumes can be stored in the interlabial space, if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

The individual components which may be suitable for the various embodiments of the interlabial device 20 of the present invention will now be looked at in greater detail with reference to FIGS. 1–3.

The topsheet 42 comprises a first liquid pervious component. The topsheet 42 should be compliant, soft feeling, and non-irritating to the wearer's skin. Further, the topsheet 42 is liquid pervious permitting liquids (e.g., menses and/or urine) to readily penetrate through its thickness. A suitable topsheet 42 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, rayon, polypropylene, or polyethylene fibers) or from a combination of natural and synthetic fibers.

A suitable topsheet 42 for use in the present invention is a nonwoven material formed of rayon fibers with a basis weight of about 18 g/m² and is available from Veratec of Walpole, Mass. sold under the designation grade 9313709070. This material is particularly suitable for use as a topsheet 42 because it is a biodegradable material.

As used herein, the term "biodegradable materials" refers to a material having greater than or equal to about 70% biodegradation (percentage of theoretical carbon dioxide evolution) after 28 days when measured according to the Sturm Test which has been designated Method 301B by the Organization for Economic Cooperation and Development. Preferably, the materials comprising the present invention have a biodegradation of greater than about 80% and, more preferably, biodegradation is greater than or equal to about 90%.

The topsheet 42 may also comprise an apertured formed film. Apertured formed films are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. A preferred formed film topsheet for the present invention is the formed film described in one or more of the above patents and marketed on sanitary napkins by The Procter & Gamble Company of Cincinnati, Ohio as the "DRI-WEAVE" topsheet.

Another suitable topsheet 42 for the present invention is made in accordance with U.S. Pat. Nos. 4,609,518 and 4,629,643 both issued to Curro et al. on Sep. 2, 1986 and Dec. 16, 1986, respectively. Such a formed film is manufactured by Tredegar Corporation of Terre Haute, Ind.

In a preferred embodiment of the present invention, the body surface of the formed film topsheet is hydrophilic to help liquids transfer through the topsheet 42 faster than if the body surface was not hydrophilic so as to diminish the likelihood that menstrual fluid will flow off the topsheet 42 rather than flowing into and being absorbed by the absorbent core 44. The body surface of the topsheet 42 can be made hydrophilic by treating it with a surfactant such as is described in U.S. Pat. No. 4,950,254 issued to Osborn, III. In a preferred embodiment, surfactant is incorporated into the polymeric materials of the formed film topsheet.

The inner surface of topsheet 42 may be secured in contacting relation with an underlying absorbent layer. This contacting relationship results in liquid penetrating topsheet 42 faster. The topsheet 42 may be kept in a contacting relationship with an underlying layer by bonding the topsheet 42 to the underlying layer. However, it is not absolutely necessary to bond the face of the topsheet 42 to the face of the underlying layer. The topsheet 42 can be maintained in contact with an underlying absorbent component, by entangling the fibers of the underlying layer with the topsheet, by fusing the topsheet 42 to an underlying absorbent layer by a plurality of discrete individual fusion bonds, or by any means known in the art.

It is not necessary that the topsheet 42 comprise a layer or material which is separate or distinct from the absorbent core 44. The topsheet 42 and absorbent core 44 may consist of one unitary structure in which the body-contacting surface of the absorbent core 44 will serve as the liquid pervious topsheet 42. In such an embodiment, the liquid pervious body contacting surface may be hydrophilic or treated so as to render it hydrophilic such that fluids readily penetrate through the surface and into the interior of the absorbent core 44. Additionally, the unitary topsheet 42 and absorbent core 44 may be provided with a pore size, capillary, or hydrophilicity gradient to assist in the absorption and retention of fluids in the interior of the absorbent core 44.

The absorbent core 44, which is best seen in FIG. 2, is positioned between the topsheet 42 and the backsheet 38. The absorbent core 44 provides the means for absorbing exudates such as menses and other body fluids. The absorbent core 44 preferably is generally compressible, conformable, and non-irritating to the user's skin.

The absorbent core 44 may comprise any suitable material that is capable of absorbing and/or retaining liquids (e.g. menses and/or urine). Preferably, the absorbent core 44 has the same general shape as the overall absorbent interlabial device 20. The absorbent core 44 (and the overall absorbent interlabial device 20) may be manufactured in a wide variety of shapes. Non limiting examples of shapes for the absorbent core 44 when viewed from the top as in FIG. 1 include ovoid, elliptical, trapezoidal, rectangular, triangular, diamond-shaped or any combination of the above. As shown in FIG. 1, the preferred shape for the absorbent core 22 and the overall absorbent interlabial device 20 is generally ovoid or elliptical.

The absorbent core 44 be manufactured from a wide variety of liquid-absorbent materials commonly used in absorbent articles such as comminuted wood pulp which is generally referred to as airfelt. Examples of other suitable absorbent materials include cotton fibers or cotton lintels, creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers (in fibrous and particulate form); absorbent gelling materials; or any equivalent material or combinations of materials, or mixtures of these. Preferred absorbent materials comprise folded tissues, cotton batts, woven materials, nonwoven webs, rayon including needle punched rayon, and thin layers of foam. The absorbent core 44 may comprise a single material. Alternatively, the absorbent core 44 may comprise a combination of materials.

A particularly preferred material for the absorbent core 44 is batt of rayon or a rayon/cotton blend. A tri-lobed rayon known as GALAXY rayon available from Courtaulds Fibers, Inc. of Axis, Ala. has been found to work well for the material comprising the absorbent core 44.

The backsheet 38, which is best shown in FIGS. 2 and 3, prevents the exudates absorbed and contained in the absorbent core 44 from wetting articles and/or body parts which may contact the absorbent interlabial device 20 such as pants, pajamas, undergarments, pubic hair, the wearer's thighs, etc. The backsheet 38 should be flexible and impervious to liquids (e.g., menses and/or urine).

The backsheet 38 is impervious to liquids (e.g., menses and/or urine) and is preferably flexible. As used herein, the term "flexible" refers to materials which are compliant and will readily conform to the general shape and contours of the human body. The backsheet 38 also provides protection for the wearer's fingers as the absorbent interlabial device 20 is inserted, or as the device is optionally removed with the fingers.

The backsheet 38 may comprise a woven or nonwoven material, polymeric films such as thermoplastic films of polyethylene or polypropylene, composite materials such as a film-coated nonwoven material, or organic material such as a collagen film. The backsheet may be made from a polyethylene film having a thickness of from about 0.012 mm (0.5 mil) to about 0.051 mm (2.0 mils). An exemplary polyethylene film is manufactured by Clopay Corporation of Cincinnati, Ohio, under the designation P18-0401. The backsheet may permit vapors to escape from the device 20 (i.e., be breathable) while still preventing exudates from passing through the backsheet.

Preferably, the backsheet 38 is dispersible and/or dissolvable in water. Polyvinyl alcohol (including co-polymers of polyvinyl alcohol) has been found to be suitable as a material for a dissolvable backsheet 38. The polyvinyl alcohol may be coated with a tissue, with a wax or other hydrophobic coating to reduce the rate at which it dissolves in water. This allows the backsheet 38 to maintain its integrity during use, while retaining the ability to dissolve in water during disposal of the device 20.

The term "dispersible" as applied herein to an absorbent interlabial device or a component thereof refers to an article or material which will disperse into at least two fragments in mildly agitated water. Such a device will break into pieces in a conventional toilet and/or domestic plumbing system, and will ultimately be effectively processed though a sewage treatment system. The term "dissolvable" as applied herein to an absorbent interlabial device or a component thereof refers to an article or material which will at least partially dissolve and essentially assume liquid form or otherwise be indistinguishable to the naked eye from the liquid medium in which it is dissolved.

The components of the absorbent interlabial device 20 described above (topsheet 42, backsheet 38, absorbent core 44) can be assembled in any suitable manner. In the preferred embodiment shown in FIGS. 1–3, the components of the interlabial device portion are assembled in a "sandwich" configuration with the components sized so that the edges of the topsheet 42 and backsheet 38 extend outward beyond the edges of the absorbent core 44. The topsheet 42 and backsheet 38 are preferably at least partially peripherally joined using known techniques. As shown in FIGS. 1 and 2, the topsheet 42 is preferably secured to backsheet 38 along a seam, such as seam 60. Seam 60 is preferably liquid impervious. The seam 60 can be formed by any means commonly used in the art for this purpose such as by gluing, crimping, or heat-sealing. The seam 60 and the area of the interlabial device 20 in the vicinity of the seam 60 should be soft, compressible, and conformable. If the seam 60 and surrounding area are too stiff or non-compressible, the wearer may experience discomfort when wearing the interlabial device 20.

The term "joined," as used herein, encompasses configurations in which an element is directly secured to another element by affixing the element directly to the other element; configurations in which the element in indirectly secured to the other element by affixing the element to intermediate member(s) which in turn are affixed to the other element; and configurations in which one element is integral with the another element, i.e., one element is essentially part of the other element.

The components of the absorbent interlabial device 20 can be joined together by adhesives, stitching, heat and/or pressure bonds, dynamic mechanical bonds, ultrasonic bonds, intermingling or entanglement of the fibers or other structural elements comprising the components of the absorbent interlabial device 20, such as by meltblowing the fibers comprising one component onto another component, extruding one component onto another, or by any other means known in the art. The components of the absorbent interlabial device 20 may be joined with water soluble adhesives in order to increase the tendency of the device 20 to disperse into a plurality of fragments in mildly agitated water (such as in a toilet).

Preferably, the interlabial absorbent device 20 of the present invention is toilet-disposable. The term "toilet-disposable" as used herein includes the following characteristics of an absorbent interlabial device: flushability, dispersibility, settleability, disintegrateability, and biodegradability. As used herein the terms "flushable" and "flushability" refer to a product's ability to pass though typically commercially available household toilets and plumbing drainage systems without causing clogging or similar problems that can be directly associated with the physical structure of the product. It is recognized, however, that there can be many differences between the various types of toilets available. Therefore, for the purposes of the appended claims, a test to determine the flushability of a catamenial product, such as an absorbent interlabial device, is set out in the TEST METHODS section of this specification.

"Settleability" refers to the tendency of an absorbent interlabial device, such as absorbent interlabial device 20 to eventually settle to the bottom of a septic tank or other sewage treatment system rather than to float on the surface of such tanks or sewage being processed.

Preferably, the absorbent interlabial device 20 of the present invention is toilet-disposable and will disperse into at least two fragments within two hours of exposure to mildly agitated room temperature water as described in the Water Dispersion Test in the TEST METHODS section, below. More preferably, the interlabial absorbent device 20 will be dispersed into a plurality of fragments within about 60 minutes or, even more preferably within about 30 minutes and most preferably, within about 15 minutes as measured by the Water Dispersion Test. Preferably, the product will break into fragments which are smaller than about 6 in$^2$, more preferably smaller than about 2 in$^2$, most preferably smaller than about 1.5 in$^2$.

In particularly preferred embodiments of the present invention, each of the components of the interlabial absorbent device 20 will disperse into a plurality of fragments when immersed in mildly agitated water. Alternatively, the components of the absorbent interlabial device 20 may separate from each other without themselves breaking into a plurality of fragments (e.g. the topsheet 42, backsheet 38, and core 44 may break apart from each other while each otherwise remaining intact).

Preferably, the absorbent interlabial device 20 comprises biodegradable materials. While biodegradable materials are preferred for the absorbent interlabial device 20, it is not necessary that each and every material used be biodegradable. For example, the device 20 may comprise superabsorbent particles which do not biodegrade, and this will not affect the ability of the overall device 20 to remain toilet-disposable and to be effectively processed in a sewage treatment system.

The absorbent interlabial device 20 of the present invention in its fully assembled configuration comprises at least one axis of preferred bending A. The axis of preferred bending A is preferably located generally along the longitudinal centerline L of the absorbent interlabial device 20. The axis of preferred bending A is a line or axis along which the absorbent interlabial device 20 will tend to bend or fold when subjected to compressive forces F directed inwardly in the transverse direction at the sides 32 of the device 20. The axis of preferred bending A may result naturally from the product configuration, or the device 20 may be imparted with a weakened axis or region in any or all of the topsheet 42, backsheet 38 and core 44 to create the axis of preferred bending A. Such a weakened axis may be created by any variety of known techniques such as scoring, pre-folding, slitting, or the like. The absorbent interlabial device 20 may comprise a region of preferred bending made up of a plurality of axes of preferred bending. Any number of such axes may comprise such a region of preferred bending up to an infinite number.

Figure 4:
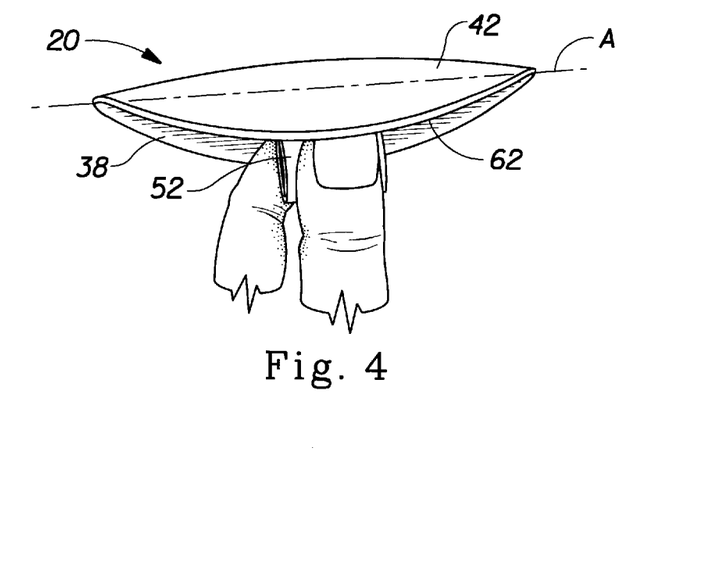
FIG. 4 shows the absorbent interlabial device of the present invention folded along the axis of preferred bending and being grasped for insertion by the wearer's fingers.

The absorbent interlabial device 20 is folded along the axis of preferred bending A, as shown in FIG. 4, prior to insertion within the wearer's interlabial space. Once inserted, the device 20 will preferably tend to unfold slightly keeping the topsheet 42 of the device 20 in contact with the inner walls of the wearer's labia. The device 20 may be resiliently biased slightly along the axis of preferred bending A to increase the tendency of the device 20 to unfold. This allows the folded device 20 to act as a "spring" under both wet and dry conditions and, consequently, to increase the tendency of the topsheet 42 of the device to remain in contact with the inner surfaces of the labia when the absorbent interlabial device 20 is in place. A device 20 constructed according to the preferred embodiment described above, however, does not necessarily require any additional structural features to provide the ability to maintain such contact. The naturally moist surfaces of the labia will have a tendency to adhere to the material comprising the topsheet 42 further tending to keep the device 20 in contact with the inner surfaces of the labia.

The absorbent interlabial device 20 described herein is both flexible and compressible. Flexibility and compressibility are important to product comport. If the absorbent interlabial device 20 is too flexible, the device is not conveniently or easily placed between the folds of the labia, if it is too stiff, the device is uncomfortable and when the user is in a sitting position, the product can be forced forward against the clitoris causing discomfort.

The absorbent interlabial device 20 of the present invention is believed to offer several advantages over previous interlabial pads. Devices constructed with the size ranges and preferred shapes described above have been found to be particularly suited for reliable insertion by a variety of wearers. Additionally, the device 20 described above have been found to be particularly effective at catching clots which may be formed from menstrual discharges. This clot catching attribute is believed to be enhanced by the generally flat topsheet 42 of the device 20 which is folded along the axis of preferred bending A in use. The folded configuration of the device 20 when properly sized as described above allows for consistent coverage of the walls of the labia and the vaginal introitus. Such coverage substantially reduces the incidence of "by-pass" around the device 20 by menstrual or other bodily discharges which are exhibited by previous interlabial pads.

Superior performance in acquiring menstrual discharges, and clots in particular, is demonstrated by an absorbent interlabial device 20 of the present invention as described above in which the topsheet 42 and the absorbent core 44 comprise rayon.

The preferred shape of the absorbent interlabial device 20 shown in FIGS. 1–3 (i.e. one in which the device is tapered at the ends) allows the device to easily and comfortably fit the wearer's interlabial space. A device 20 with such a tapered shape, when folded along an axis of preferred bending A (as in FIG. 4) will have a profile in which highest point along the axis of bending A (as measured in the "z"-direction) is in the vicinity of the center of the device 20 rather than at the ends.

The liquid impervious backsheet 38 of the absorbent interlabial device 20 is also responsible for improved product performance. As described above, the backsheet reduces the likelihood of body or clothing soiling from discharges which are absorbed by the device 20. Additionally when the device 20 is folded along the axis of preferred bending A, the backsheet 38 will form a recess 62 which protects the wearer's fingers from soiling when the device 20 is inserted.

Previous interlabial pads have not combined the attributes of the device 20 of the present invention to obtain the performance and comfort results described herein.

Several previous pads consisted of a small generally cylindrically shaped absorbent material which is inserted into the interlabial space. These devices were not provided with a liquid impervious backsheet. Consequently, they are characterized by a less cleanly insertion and removal and may be associated with increased panty and body soiling in comparison to the present device 20. Other previous pads did include an impervious backsheet, but the pads were much larger than the device 20 of the present invention and included significant portions which resided externally to the interlabial space. Such designs may also lead to increased body soiling as discharged bodily fluids migrate to the external surfaces of such pads. Additionally, the interlabial device 20 of the present invention is believed to offer comfort advantages (e.g. reduced wearing awareness) as compared to the above-described larger prior art pads.

It has been found during development of the present invention that the absorbent interlabial device 20 better conforms to the labial vault than previously available interlabial pads. Additionally, the generally flat and folded configuration of the absorbent interlabial device 20 of the present invention is found to give a better visual indication to users as to how to insert and use the device. Therefore, the device 20 of the present invention is associated with an easier and more accurate insertion as compared to previous interlabial pads.

The absorbent interlabial device 20 is preferably provided with an optional removal tab 52 joined to the backsheet 38. The tab 52 may be made of a variety of materials and need not be absorbent. The tab 52 may be formed from a nonwoven material which is heat bonded to a tissue layer. A suitable nonwoven material is known as COROLIND and is available from Corovin, GmbH, Peine, Germany. A suitable airlaid tissue is available from Merfin Hygenic Products, Ltd., of Delta, British Columbia, Canada, having a basis weight of about 61 g/m$^2$ and having the designation grade number 176.

The tab 52 may be of any suitable size which provides for a convenient finger grip during insertion and, optionally, removal of the device 20. In the preferred embodiment shown in FIGS. 1–3, the tab 52 is about 20 mm long, and about 13 mm in height (i.e. measured in the "z"-direction after attachment).

The tab 52 is preferably joined to the surface of the backsheet 38 which faces away from the topsheet 42. The tab 52 provides a location for the wearer to grasp the device 20 during insertion. The absorbent interlabial device 20 is designed to be expelled by urination. The tab 52, however, may provide an alternative mechanism for removal of the device 20 (i.e. removal with the fingers).

As previously discussed, the absorbent interlabial device 20 of the present invention is designed to be placed within the interlabial space of a wearer. To use the absorbent interlabial device 20 of the present invention, the wearer grasps the tab 52 of the device 20. If the device 20 is not provided with a tab 52, the wearer may hold the folded device 20 at the sides 32 and begin insertion. The device 20 is then further inserted by pushing with a finger or fingers in the recess 62 formed by the folded backsheet 38.

Figure 5:
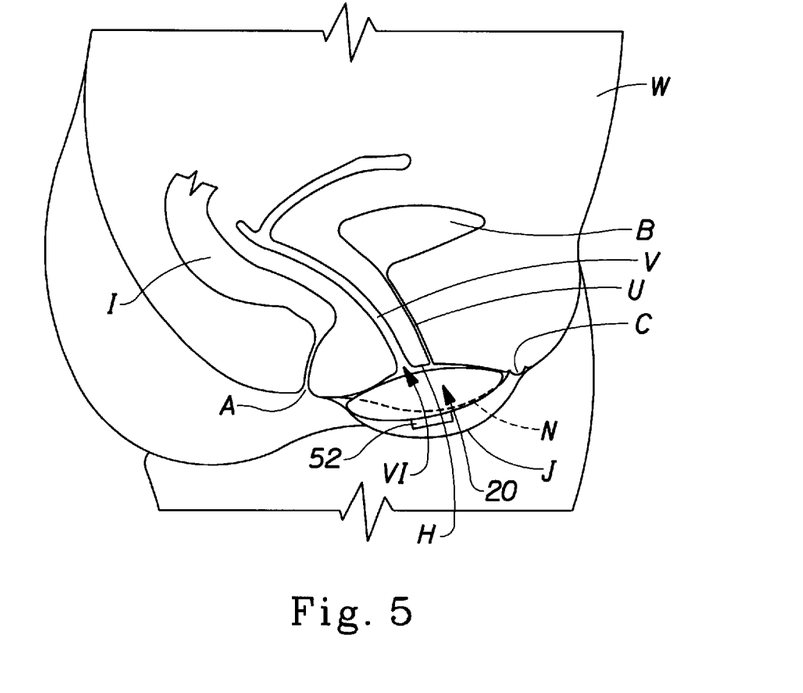
FIG. 5 is a cross-sectional saggital view of a human female wearer showing the placement of the absorbent interlabial device in the wearer's interlabial space.

As shown in FIG. 4, the folded device 20 forms a recess 62 within the folded backsheet 38 which covers the tips of the wearer's fingers during insertion. This feature provides for a hygienic insertion of the absorbent interlabial device 20 of the present invention. The wearer may assume a squatting position during insertion to assist in spreading the labial surfaces. FIG. 5 shows a preferred embodiment of the absorbent interlabial device 20 of the present invention inserted into the interlabial space of a wearer W. The urogenital members shown in FIG. 5 include the bladder B, the vagina V, the urethra U, the clitoris C, the large intestine I, the anus A, the vaginal introitus VI, the hymenal ring H) the labia minora N, and the labia majora J. FIG. 5 shows the relationship of these anatomical features of the wearer W to the absorbent interlabial device 20 when the device is properly inserted for use. Once the absorbent interlabial device 20 is inserted, the topsheet 42 tends to adhere to the inside surfaces of the labia. When the wearer is standing, the labial walls close more tightly around the folded absorbent interlabial device 20.

The interlabial device 20 is preferably at least partially retained in place by exerting a slight laterally outwardly-oriented pressure on the inner surfaces of the wearer's labia minora, labia majora, or both. Additionally, the product may also be held by attraction of naturally moist labial surfaces to the material comprising the topsheet 42. Optionally, the topsheet 42 of the device 20 may be provided with a bio-compatible adhesive to assist the adhesion of the device 20 to the inside surfaces of the wearer's labia. The strength of such an adhesive should be selected to assist the absorbent interlabial device 20 in staying in place, while still allowing for reliable, and comfortable removal of the device from the wearer's interlabial space.

The absorbent interlabial device 20 can be worn as a "stand alone" product. Additionally, superior performance in reducing body and clothing soiling over extended periods of wear time (such as overnight) can be obtained by using the absorbent interlabial device 20 as part of a "system" of feminine hygiene products. One such system which is effective in reducing soiling is an absorbent interlabial device, such as absorbent interlabial device 20, which is worn simultaneously with a sanitary napkin, such as sanitary napkin 70 (shown in FIG. 6).

Figure 6:
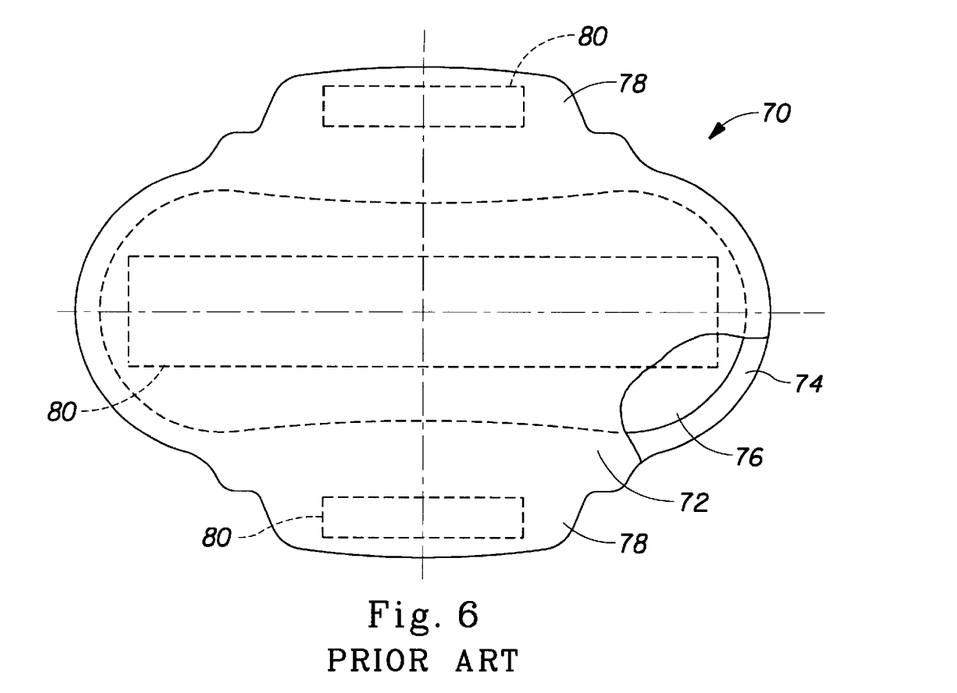
FIG. 6 is a typical prior art sanitary napkin which may be used in a method of using a system of feminine hygiene products or as part of a feminine protection kit of the present invention.

Such a system of an interlabial device in combination with a sanitary napkin is more effective than either a sanitary napkin or an interlabial pad worn alone. The absorbent interlabial device used in the system of the present invention may, and preferably does, have all of the preferred attributes of the absorbent interlabial device 20 described above. The sanitary napkin 70 of the present system may be any suitable conventional sanitary napkin. The sanitary napkin 70 preferably comprises at least a liquid pervious topsheet 72, a liquid impervious backsheet 74 joined to said topsheet, and an absorbent core 76 positioned between the topsheet 72 and the backsheet 74. Additionally, the sanitary napkin 70 preferably includes a pressure sensitive adhesive 80 disposed on the garment facing side of the backsheet 74. The adhesive 80 allows the sanitary napkin 70 to be adhered to the crotch portion of the wearer's undergarments. When the undergarments are worn in their usual wearing position, the sanitary napkin 70 will rest adjacent the pudendal region of the wearer's body. The sanitary napkin 70 may also be provided with additional features commonly found in sanitary napkins, including "wings" or "flaps" such as wings 78. A suitable sanitary napkin for use in the above-described system is the "ALWAYS" Ultra thin Maxi with Wings sanitary napkin which is manufactured and packaged by the Procter & Gamble Company of Cincinnati, Ohio under one or more of U.S. Pat. Nos. 4,342,314; 4,463,045; 4,556,146; B1 4,589,876; 4,687,478; 4,950,264; 5,009,653; 5,267,992; 5,413,568; 5,460,623; 5,462,166; 5,489,283; 5,569,231; and U.S. Pat. No. Re. 32,649. Other sanitary napkins are also acceptable, such as those without wings 78 or those which are not of the "Ultra-thin" type.

In order to use an absorbent interlabial device and a sanitary napkin as a system of feminine hygiene products, the wearer inserts the absorbent interlabial device into her interlabial space and places a sanitary napkin in the crotch portion of a panty-type undergarment. These two steps may be performed in either order. Some women will prefer to place the sanitary napkin in the panty crotch first in order to catch and absorb and drops of menstrual flow which might be released prior to the time that the absorbent interlabial device can be inserted. Other women will chose to first insert the absorbent interlabial device. After the absorbent interlabial device is inserted and the sanitary napkin is positioned in the undergarment crotch, the undergarment is pulled up into its usual wearing position. Consequently, the sanitary napkin will rests adjacent the pudendal region of the wearer's body and will be worn simultaneously with the absorbent interlabial device.

Preferably, the absorbent interlabial device used with the above-described system is changed each time the wearer urinates. The associated sanitary napkin may be worn during for longer periods of time (i.e. beyond the changing of the absorbent interlabial device) because the bulk of the bodily fluids will be deposited on and absorbed by the interlabial device as opposed to the sanitary napkin. Particularly if the absorbent interlabial device 20 is provided with a tab 52 for removal, some women will prefer to remove the absorbent interlabial device 20 prior to urination, then subsequently re-insert the same device 20 if it has not yet absorbed near its full capacity.

Figure 7:
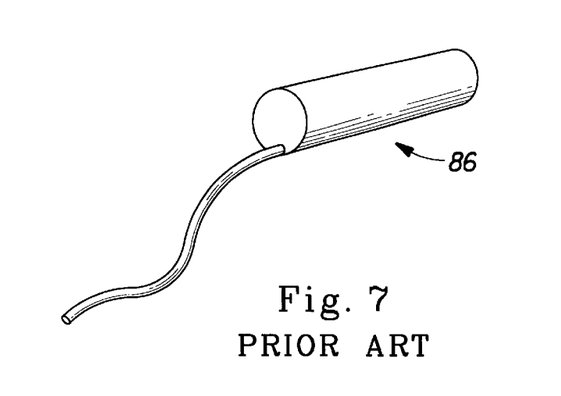
FIG. 7 is a typical prior art tampon which may be used in a method of using a system of feminine hygiene products or as part of an additional feminine protection kit of the present invention.

The sanitary napkin and the absorbent interlabial device of the above-described system may be packaged in a common package as a feminine hygiene "kit." Such a kit facilitates use of the system of the present invention. Preferably, the packaging associated with such a kit will include instructions on how to use the absorbent interlabial device and the sanitary napkin according to the above-described method as a system of feminine hygiene products. An alternate suitable system of feminine hygiene products comprises the absorbent interlabial device 20 of the present invention used simultaneously with an absorbent tampon, such as tampon 86 shown in FIG. 7. The absorbent tampon of his system of feminine hygiene product may be any suitable conventional catamenial tampon including any of the tampons sold under the trademark "TAMPAX" and distributed by The Procter & Gamble Company of Cincinnati, Ohio. The tampon used may be either of the applicator insertion or digital insertion type and any suitable applicator known in the art may be used. The tampon is first inserted into the vaginal cavity of the wearer. Following insertion of the tampon, the absorbent interlabial device is inserted into the interlabial space of the wearer. The interlabial device and the tampon are then worn simultaneously for a period of time. The absorbent interlabial device may be removed and changed each time the wearer urinates, or may be removed then re-inserted subsequent to urination.

Similarly, the absorbent tampon and the absorbent interlabial device 20 of this system may also be packaged in a common package as a feminine hygiene kit. This kit facilitates use of the alternate system of the present invention.

Systems and associated kits of the present invention may also comprise the simultaneous use of an absorbent interlabial device, tampon, and sanitary napkin. Kits comprising all three types of feminine hygiene products may also be packaged in a common package and include appropriate instructions for use of such systems.

In addition to the systems described above, the absorbent interlabial device 20 may be worn simultaneously with a pantiliner, or incontinence pad for menstrual or incontinence use. The absorbent interlabial device 20 described above may be combined and packaged with a pantiliner, an incontinence pad, or a sanitary napkin to form a feminine urinary incontinence kit. Such an incontinence kit preferably includes appropriate packaging material instructing the wearer as to how to use the feminine hygiene products for light incontinence protection. The interlabial device 20 can be worn in conventional panties, or it can be used with menstrual shorts.

Numerous alternative embodiments of the absorbent interlabial device of the present invention are possible. For example, these products are designed to be removed by urination, although an alternative extraction string or loop may be used. These products may also be used with emollients and/or medicinal treatments. For example, a suitable emollient for use on the absorbent interlabial device 20 of the present invention is comprised of about 50% petrolatum, about 39% Cetearyl Alcohol, and about 15% Ceteareth-10. An emollient coating of about 0.03 g/pad has been found to be suitable.

The absorbent interlabial device 20 of the present invention may be provided with a visual indication on the center of the topsheet 42 designating the area of greatest absorbent capacity of the device 20. Such an indication may consist of a differently colored region such as a pink oval. The indication may be about 12 mm wide and about 20 mm long. The absorbent interlabial device 20 may also be provided with a visual change indication. In other words, the device 20 may have a ring, bonding pattern, compression lines, or other visual indicator provided on the surface of the topsheet 42 at a predetermined distance inboard from the seam 60. When absorbed bodily discharges reach the visual change indication or outboard of the change indication, the user knows to replace the absorbent interlabial device 20. Such a change indication is particularly useful to users who remove the device 20 prior to urination and then re-insert the same device 20 if it has not yet reached its absorbent capacity.

Figure 8:
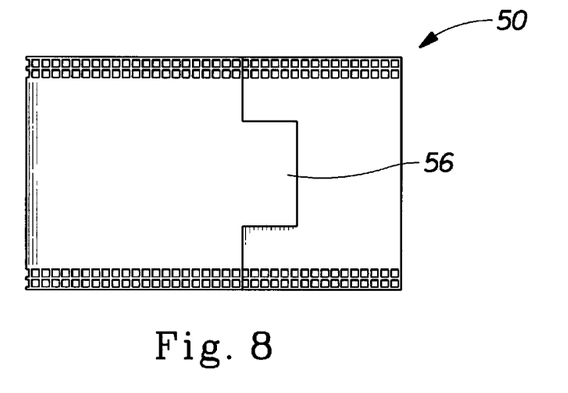
FIG. 8 is front view of an individual package for the interlabial device in an unopened condition.
Figure 9:
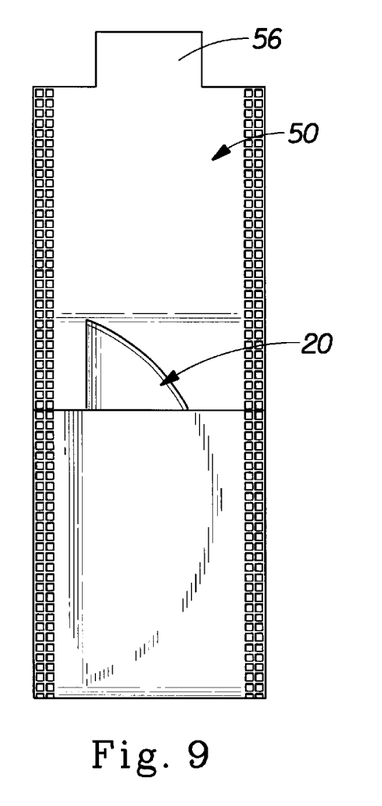
FIG. 9 is front view of the individual package in an opened condition with the folded interlabial device inside.

If desired, the absorbent interlabial device 20 may be packaged in an individual package, such as the package 50 shown in FIGS. 8 and 9. The individual package 50 may be comprised of a number of suitable materials, including films and toilet-disposable materials. In FIGS. 8 and 9, the package 50 is made of a film which is frangibly sealed at the edges. The package 50 is provided with an opening tab 56 which can be of any suitable configuration. Suitable methods for frangibly sealing packages are described in U.S. Pat. No. 4,556,146 issued to Swanson and U.S. Pat. No. 5,462,166 issued to Minton, et al. Suitable tabs for such a package U.S. Pat. No. 5,413,568 issued to Roach, et al.

The following examples are presented to provide a more detailed understanding of the benefits which are achieved from the absorbent interlabial device, the methods and the kits of the present invention. The EXAMPLES are intended to be representative, and are not intended to specifically limit the scope of the invention.

EXAMPLES

Base Pad 1 is a commercially available "ALWAYS" ultra thin Maxi sanitary napkin. Base Pad 2 is a commercially available "ALWAYS" ultra thin Maxi with Wings sanitary napkin. Both are manufactured by The Procter & Gamble Company of Cincinnati, Ohio.

Interlabial Pad 1 is the commercially "IN-SYNC MINI-FORM" interlabial pad (also previously known as the "FRESH 'N FIT PADETTE") manufactured by A-Fem (previously known as Athena Medical Corp.) of Portland, Oreg.

Interlabial Pad 2 is an absorbent interlabial device of the present invention constructed as described above. The topsheet is 100% rayon. The core is 50% cotton and 50% Galaxy Rayon. The backsheet is a polyethylene film manufactured by Clopay Corporation of Cincinnati, Ohio, under the designation P18-0401. The pad has a removal tab constructed of a nonwoven material heat bonded to a tissue layer. The nonwoven material is COROLIND available from Corovin, Gmbl Peine, Germany. The tissue is an airlaid tissue is available from Merfin Hygenic Products, Ltd., of Delta, British Columbia, Canada, having the designation grade number 176. The pad caliper is about 5.5 mm, the width about 40 mm, and the length about 85 mm. Each pad is coated with about 0.03 g of emollient comprised of about 50% petrolatum, about 39% Cetearyl Alcohol, and about 15% Ceteareth-10.

Table 1 below describes systems of pads which are used by groups of menstruating women for one complete menstrual cycle. The below described systems are used exclusively during the cycle. The participants are instructed to change all pads each time they urinate (about every 2–3 hours). The table reports incidence of panty soiling associated with each system or pad.

TABLE 1

| Base Pad | Pad 1 | Pad 1 | Pad 1 | Pad 2 | Pad 2 | Pad 2 |
|---|---|---|---|---|---|---|
| Interlabial Pad | None | Pad 1 | Pad 2 | None | Pad 1 | Pad 2 |
| Number of Women | 31 | 38 | 56 | 45 | 20 | 65 |
| Panty Soiling | 35% | 22% | 13% | 19% | 12% | 6% |

As is demonstrated above, significant performance improvements are obtained from the method and kit of the present invention, and from the interlabial device of the present invention.

TEST METHODS

Absorbent Capacity

Absorbent capacity may be determined as follows. The test is performed on samples that have been conditioned by leaving them in a room at 50% relative humidity and at 73° F. for a period of two hours prior to the test, The test should be performed under similar conditions.

The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and laid horizontally on a wire mesh screen having square openings 0.25 inches by 0.25 inches (0.64 cm by 0.64 cm) for five minutes to allow the saline to drain out to the article. Both sides of the article are then covered with absorbent blotters, such as the filter paper #631 available from the Filtration Science Corp., Eaton-Dikeman Division of Mount Holly Springs, Pa. A uniform 1 pound per square inch load is placed over the article to squeeze excess fluid out. The absorbent blotters are replaced every 30 seconds until the amount of fluid transferred to the absorbent blotters is less than 0.5 grams in a 30 second period. Next, the article is weighed to the nearest 0.1 gram and the dry weight of the article is subtracted. The difference in grams is the absorbent capacity of the article.

Water Dispersion Test

Apparatus

| | |
|---|---|
| Shaker | Junior Orbit Shaker available from Lab Line Instruments of Melrose Park, Illinois. |
| Thermometer | 30 to 120° F. with 1 degree divisions |
| Timer | Digital stopwatch |
| Jar with Lid | 16 oz. Glass jar with lid. |
| Conditioned Room | Temperature and humidity should be controlled to remain within the following limits:<br>Temperature: 73 ± 3° F. (23° C. ± 2° C.)<br>Humidity: 50 ± 2% Relative Humidity |

Test Setup
1. Fill the glass jar with 300 ml. of 73+3° F. tap water.
2. Set the speed on the Junior Orbit Shaker to 250 rpm according to the manufacturer's directions.

Procedure
1. Hold a sample (e.g. an absorbent interlabial device 20) 3 to 4 inches (7.6 to 10.2 centimeters) above the surface of the water in the jar. Gently drop the sample onto the water surface.
2. Place the lid on the jar.
3. Place the jar into the Junior Orbit Shaker such that the jar is oriented on its side.
4. Start the Junior Orbit shaker with the on/off switch, starting the timer when the shaker is turned on.
5. Record the time required until the sample separates into at least two pieces. Separation does not include the disassociation of a few individual fibers from an otherwise intact sample. The time is the total time the sample is being shaken.
6. Repeat steps 1 through 5 with an additional 3 samples.

Calculation and Reporting

Calculate and report the mean and standard deviation of the water dispersibility time for the four samples tested.

Flushability Test

Overview

As noted above, the terms "flushable or flushability" refer to a product's capacity to pass through typical commercially available household toilets and plumbing drainage systems without causing clogging or similar problems that can be directly associated with the physical characteristics of the product. For the purpose of the appended claims, catamenial products are evaluated for flushability via relative ease of toilet bowl and trap evacuation and subsequent transport through a simulated plumbing system. The flushability of such a device should be measured by the following test procedure.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of catamenial product (that is, the interlabial device or other device to be tested) with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 10:
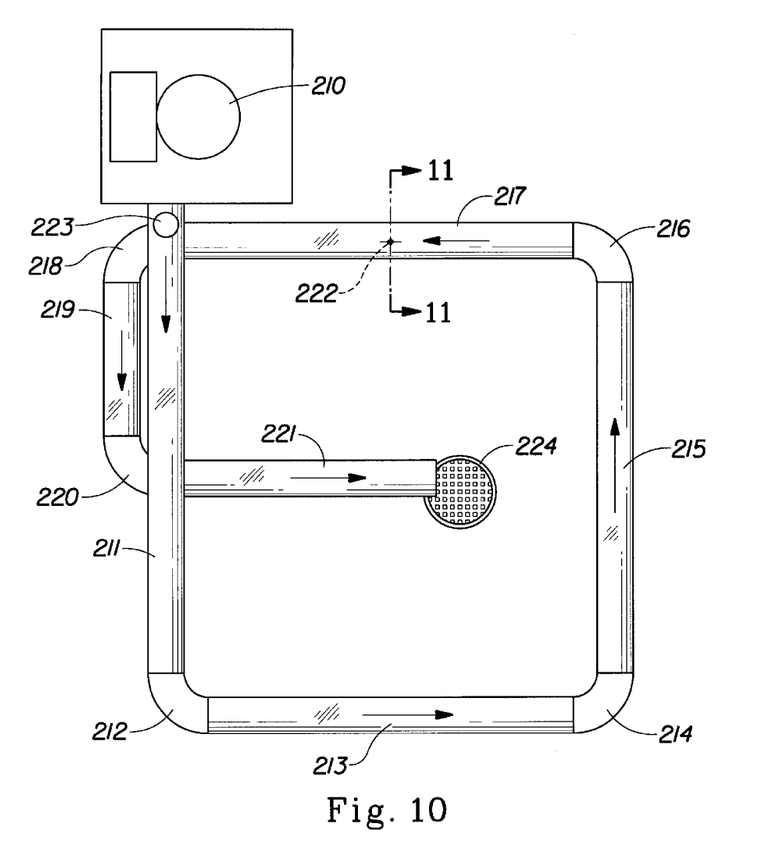
FIG. 10 is a plan view of an apparatus suitable for flushability determination according to the method described in the TEST METHODS section, below.
Figure 11:
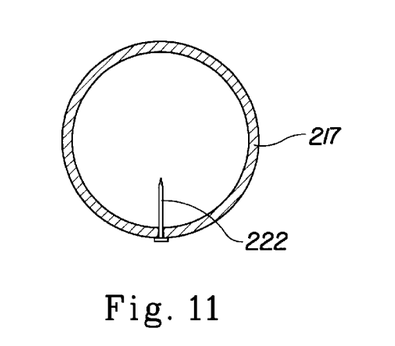
FIG. 11 is a cross-section of the flushability apparatus of FIG. 10 taken along line 11—11 thereof.

An apparatus suitable for the flushability test is shown in plan view in FIG. 10. The apparatus includes:

a 3.5 gallon (13.2 liter) water saver siphon vortex toilet referred to as 210 (additional toilets can also be attached to the piping layout shown in FIG. 10 to evaluate the behavior of test samples using different flushing mechanisms such as commercial, pressure toilets);

approximately 59 feet (18 meters) of 4 inch (10 cm) inside diameter acrylic pipe (As can be seen from FIG. 10, the piping is assembled in roughly a square configuration having linear runs 211, 213, 215, 217, 219, 221 approximately 10 feet (3 meters) long);

a cast iron tee 223 slightly downstream of the toilet 210 that is open to the atmosphere for venting;

five cast iron ninety degree elbows 212, 214, 216, 218, and 220;

a snag 222 positioned vertically (FIG. 11) approximately 15 feet from the pipe's terminal end and approximately 1 inch (2.5 cm) long; and a screen 224 (No. 4 Tyler sieve) to capture solid effluent for evaluation of disintegration.

The apparatus used for this method is set up to be equivalent to ANSI Standard Al 12.19.2M-1990 for Vitreous China fixtures. The piping is plumbed to provide a drop of 0.25 inch per foot (2 centimeters/meter) of pipe length.

Materials

Tissue Product used in Test: standard "CHARMIN" toilet tissue manufactured by

The Procter & Gamble Company of Cincinnati, Ohio.

Synthetic Fecal Material

Prepared according to the method described below

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and a catamenial product and 6 flushes with tissue and simulated fecal matter (SFM). When it is used, the SFM is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips (or the catamenial product) are placed in the bowl at 10 second intervals. Ten seconds after the final strip or catamenial product is placed into the bowl, the toilet is flushed. The flushing sequence is described below as a series of two routines combined in the following order:

Routine #1 (To be performed first 6 times for a total of 30 flushes)
1) Flush With Tissue Only—Take a drain line blockage reading 2 minutes after the water reaches the simulated obstruction, wait 1 additional minute, and move to step 2.

2) Flush With Empty Bowl. Take a drain line blockage reading 2 minutes after the water reaches the snag point and move to step 3.
3) Flush With Tissue and Catamenial Product—Take a drain line blockage reading 2 minutes after the water reaches the snag point, wait 1 additional minute, and move to step 4.
4) Flush With Empty Bowl. Take a drain line blockage reading 2 minutes after the water reaches the snag point and move to step 5.
5) Flush With Tissue and Simulated Fecal Matter (SFM). Take a drain line blockage reading 2 minutes after the water reaches the snag point, wait 1 additional minute.

Routine #2 (To be performed 1 time)

1) Flush With Tissue Only—Take a drain line blockage reading 2 minutes after the water reaches the snag point, wait 1 additional minute, and move to step 2.
2) Flush With Empty Bowl. Take a drain line blockage reading 2 minutes after the water reaches the snag point and move to step 3.
3) Flush With Tissue Only—Take a drain line blockage reading 2 minutes after the water reaches the snag point, wait 1 additional minute, and move to step 4.
4) Flush With Empty Bowl. Take a drain line blockage reading 2 minutes after the water reaches the snag point.

Total number of flushes per sequence is 34.

If, after the second flush in the flushing sequence, the product remains in the bowl or trap after flushing, the tissue and or catamenial product is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:

1) Incidence of failure (%) of catamenial product to clear bowl and trap in one flush
2) Incidence of failure (%) of catamenial product to clear bowl and trap in two flushes
3) Incidence of product on simulated snag
4) Maximum level (%) of drain line blockage
5) Cumulative level (%) of drain line blockage over the 2 day simulated test period.

Preferably, the products described herein will completely clear the bowl at least about 70% of the time in two or fewer flushes, more preferably at least about 80% of the time in one flush, even more preferably at least about 90% of the time in one flush, and most preferably at least about 95% of the time in one flush. The products described herein will preferably have a maximum level of drain line blockage of less than or equal to about 80%. The products described herein will preferably have a cumulative level of drain line blockage over the 2 day simulated test period of less than or equal to about 50%.

Preparation of Synthetic Fecal Material

I. Materials Needed:
   Feclone synthetic fecal matter (900 grams);
      (Available from Siliclone Studio, Valley Forge, Pa. as product BFPS-7 dry concentrate)
   Tap water at 100° C. (6066 grams)

II. Equipment Needed:
   Mixer (Available from Hobart Corp., Troy, Ohio as Model A200)
   Extruder (Available from Hobart Corp., Troy, Ohio as Model 4812)
   Disposable Centrifuge tubes with screw caps (50 ml) (Available from VWR Scientific, Chicago, Ill. as Catalog No. 21-008-176)
   Water Bath to control temperature to 37° C.

III. Preparation:
   1. Pour the 100° C. water into the mixing bowl of the mixer and add the dry Feclone concentrate.
   2. Mix on low for 1 minute.
   3. Mix on medium speed for 2 minutes.
   4. After the material is well mixed, transfer to the extruder.
   5. Using an ice pick, punch a small hole in the tip of each centrifuge tube.
   6. Extrude the Feclone into the centrifuge tubes.
   7. Cap the centrifuge tubes and store in the refrigerator.
   8. Before using, put the tubes in the water bath at 38° C.

This concludes the test.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent device insertable into the interlabial space of a female wearer, said absorbent device having a length, a width, a thickness, and a longitudinal centerline, said absorbent device comprising:
   a liquid pervious topsheet;
   a liquid impervious backsheet joined to said topsheet; and
   an absorbent core positioned between said topsheet and said backsheet; wherein
      said length of said absorbent device is greater than about 60 mm and less than about 127 mm,
      said width of said absorbent device is between about 25 mm and about 40 mm,
      said width and said length of said absorbent device each exceed said thickness of said absorbent device,
      said absorbent device comprises an axis of preferred bending, such that when said absorbent device is folded along said axis and inserted into the wearer's interlabial space said topsheet of said absorbent device maintains contact with the walls of the wearer's labia.

2. The absorbent device of claim 1 wherein said length of absorbent device is between about 85 mm and about 100 mm.

3. The absorbent device of claim 1 wherein said liquid pervious topsheet comprises needle punched rayon.

4. The absorbent device of claim 1 wherein said absorbent core comprises rayon.

5. The absorbent device of claim 4 wherein said absorbent core comprises a blend of rayon and cotton.

6. The absorbent device of claim 1 wherein said absorbent core further comprises a superabsorbent polymer.

7. The absorbent device of claim 1 wherein the time required for said absorbent device to disperse into at least two fragments as measured by the Water Dispersion Test is less than about two hours.

8. The absorbent device of claim 6 wherein the time required for said absorbent device to disperse into at least two fragments as measured by the Water Dispersion Test is less than about 1 hour.

9. The absorbent device of claim 7 wherein the time required for said absorbent device to disperse into at least two fragments as measured by the Water Dispersion Test is less than about 30 minutes.

10. The absorbent device of claim 6 wherein said liquid impervious backsheet comprises polyvinyl alcohol.

11. The absorbent device of claim 1 wherein said absorbent device is at least about 70% biodegradable.

12. The absorbent device of claim 11 wherein said absorbent device is at least about 90% biodegradable.

13. The absorbent device of claim 1 wherein said backsheet is at least about 70% biodegradable.

14. The absorbent device of claim 1 wherein said backsheet is at least about 90% biodegradable.

15. The absorbent device of claim 1 further comprising a removal tab joined to said backsheet.

16. The absorbent device of claim 1 wherein said device has a substantially ovoid planar shape.

17. The absorbent device of claim 16 wherein said device tapers to a lesser width at each end.

18. The absorbent device of claim 1 wherein said device is resiliently biased to unfold along said axis of preferred bending.

19. The absorbent device of claim 1 wherein said device is sufficiently flushable that it completely clears the bowl under the Flushability Test at least about 70% of the time in two or fewer flushes.

20. The absorbent device of claim 19 wherein said device is sufficiently flushable that it completely clears the bowl under the Flushability Test at least about 90% of the time in one flush.

21. An absorbent interlabial device insertable into the into the interlabial space of a female wearer, said absorbent device having a length, a width, a thickness, and a longitudinal centerline, said absorbent device comprising:

a liquid pervious topsheet;

a liquid impervious backsheet jointed to said topsheet; and an absorbent core positioned between said topsheet and said backsheet; and a removal tab joined to said backsheet and extending downwardly therefrom; wherein said width and said length of said absorbent device each exceed said thickness of said absorbent device, said absorbent device comprises an axis of preferred bending, such that when said absorbent device is folded along said axis and inserted into the wearer's interlabial space said topsheet of said absorbent device maintains contact with the walls of the wearer's labia.

* * * * *